United States Patent [19]

Lang et al.

[11] Patent Number: 4,995,382

[45] Date of Patent: Feb. 26, 1991

[54] WOUND DRESSING, MANUFACTURE AND USE

[75] Inventors: Stephen M. Lang, Saffron Walden; David F. Webster, Bishops Stortford, both of United Kingdom

[73] Assignee: Smith and Nephew Associated Companies Limited, United Kingdom

[21] Appl. No.: 345,099

[22] Filed: Apr. 28, 1989

Related U.S. Application Data

[63] Continuation of Ser. No. 946,362, Dec. 24, 1986, abandoned, which is a continuation of Ser. No. 812,963, Dec. 24, 1985, abandoned, which is a continuation of Ser. No. 522,415, Aug. 11, 1983, abandoned, which is a continuation-in-part of Ser. No. 516,119, Jul. 20, 1983, abandoned, which is a continuation-in-part of Ser. No. 506,501, Jun. 21, 1983, abandoned, which is a continuation-in-part of Ser. No. 396,754, Jul. 9, 1982, abandoned, which is a continuation-in-part of Ser. No. 396,732, Jul. 9, 1982, abandoned, which is a continuation-in-part of Ser. No. 345,550, Feb. 3, 1982, abandoned, which is a continuation-in-part of Ser. No. 345,488, Feb. 3, 1982, abandoned.

[30] Foreign Application Priority Data

| Feb. 13, 1981 | [GB] | United Kingdom | 8104568 |
|---|---|---|---|
| May 22, 1981 | [GB] | United Kingdom | 8115742 |
| Feb. 12, 1982 | [GB] | United Kingdom | 8204132 |
| Feb. 12, 1982 | [GB] | United Kingdom | 8204133 |
| Jun. 22, 1982 | [GB] | United Kingdom | 8218088 |
| Jul. 21, 1982 | [GB] | United Kingdom | 8221112 |
| Aug. 12, 1982 | [GB] | United Kingdom | 8223254 |

[51] Int. Cl.$^5$ .............................. A61L 15/00
[52] U.S. Cl. .................................. 128/156; 128/155
[58] Field of Search ................. 128/155, 156; 604/366, 604/369, 370, 375

[56] References Cited

U.S. PATENT DOCUMENTS

| 2,293,298 | 2/1960 | Dockstader et al. | 128/156 |
|---|---|---|---|
| 3,307,544 | 3/1967 | Gander et al. | 128/155 |
| 3,526,224 | 9/1970 | Potts | 128/156 |
| 3,543,750 | 12/1970 | Meizanis | 128/156 |
| 3,678,933 | 7/1972 | Moore et al. | 604/389 |
| 3,709,221 | 1/1973 | Riely | 128/156 |
| 3,972,328 | 8/1976 | Chen | 128/156 |
| 3,978,855 | 9/1976 | McRae et al. | 128/156 |
| 4,181,127 | 1/1980 | Linsky et al. | 128/155 |
| 4,341,207 | 7/1982 | Steer et al. | 128/155 |
| 4,649,909 | 3/1987 | Thompson | 128/155 |

FOREIGN PATENT DOCUMENTS

1280631 7/1972 United Kingdom ............... 128/155

Primary Examiner—Stephen C. Pellegrino
Assistant Examiner—Michael Rafa
Attorney, Agent, or Firm—Jacobs & Jacobs

[57] ABSTRACT

A wound dressing which comprises an absorbent layer comprising an open cell foam of a hydrophilic polymer and a wound facing layer comprising either a conformable net of elastomer coated with adhesive on its wound facing surface or an adhesive layer, pattern spread in a conformable net-like configuration, the dressing optionally also having a conformable moisture vapour transmitting outer layer; and a process for making said dressing.

10 Claims, No Drawings

WOUND DRESSING, MANUFACTURE AND USE

This is a continuation of U.S. application Ser. No. 946,362, filed Dec. 24, 1986, which is a continuation of U.S. application Ser. No. 812,963, filed Dec. 24, 1985, which is a continuation of U.S. Ser. No. 522,415, filed Aug. 11, 1983, which is a continuation-in-part of U.S. Ser. No. 516,119, filed July 20, 1983, which is a continuation-in-part of U.S. Ser. No. 506,501, filed June 21, 1983, which is a continuation-in-part of U.S. Ser. No. 396,754, filed July 9, 1982, which is a continuation-in-part of U.S. Ser. No. 396,732, filed July 9, 1982, which is a continuation-in-part of U.S. Ser. No. 345,550, filed Feb. 3, 1982, which is a continuation-in-part of U.S. Ser. No. 345,488, filed Feb. 3, 1982, all abandoned, and which all applications are incorporated herein by cross-reference.

Burns and other related wounds such as donor sites and the like present a serious problem in that they tend to produce large amounts of exudate which can cause conventional dressings to become saturated or to stick to the wound or even become infected. One method of covering such wounds has been to cover the wound with a material into which new epithelial or fibroblast growth can penetrate. Dressings of this kind are disclosed in U.S. Pat. Nos. 3,526,224, 3,648,692 and 3,939,742.

However such dressings can be extremely painful to remove and often require surgical excision. A fundamentally different approach requiring a fundamentally different type of dressing is to employ materials that are designed to reduce the propensity to adhere to the wound. Dressings of this kind are disclosed in British Patent No. 439085, French Patent No. 947609, U.S. Pat. Nos. 3,543,750, 2,923,298 and British Patent No. 778813 which later patents cover successfully used materials such as Melolin ("Melolin" is a registered Trade Mark of T. J. Smith and Nephew Limited, Welwyn Garden City, Herts. U.K.). One more recent attempt at non-adherent dressings is U.S. Pat. No. 3,709,221 which discloses a dressing having an outer microporous, liquid repellent fibrous layer, an inner macroporous fibrous layer and an absorbent intermediate layer which was also envisaged as normally being fibrous. In order to reduce the tendency of this material to adhere to the wound the inner layer had to be treated with an agent to render it non-wetted by body liquid. It is now realised that it would be desirable to provide a dressing in which the wound facing layer did not require a special treatment. As it will become apparent hereinafter it has now been discovered that by avoiding fibrous materials it is possible to produce a dressing with reduced tendency to adhere to wounds without the need for special treatments. An attempt at producing an absorbent dressing is described in U.S. Pat. No. 3,888,248 which describes a dressing fabricated from at least four sheet materials. The wound facing part of the dressing apparently consists of a grid or scrim coated with polyethylene in such manner that the polyethylene surrounds the filaments of the grid and collects any loose thread or particle that may be present in the core material. It is now realised that it is desirable to avoid the use of wound facing layers that can allow such penetration of the central layer to the wound surface. It has also been realised that it would be desirable to provide a material that was highly conformable to the wound so that it is possible to minimise the quantity of exudate between the wound surface and the dressing. U.S. Pat. Nos. 3,709,221 and 3,888,248 disclose materials which are bonded along their edges which may reflect a desire to improve conformability. The dressing of the present invention allows for bonding over the whole of the operative area while retaining flexibility.

Accordingly the present invention provides a wound dressing which consists essentially of a low wound adherency wound facing layer, and absorbent layer and optionally an outer layer characterised in that the wound facing layer comprises a conformable apertured film or a conformable net of elastomer coated with adhesive on its wound facing surface or an adhesive layer pattern spread in a conformable net-like configuration, the absorbent layer comprises a conformable hydrophilic foam and the outer layer is either absent or is a continuous moisture vapour transmitting conformable film or is a conformable elastically extensible net or is a conformable backing layer which has an adhesive layer on one surface thereof, at least one of said backing layer and said adhesive layer being continuous to provide a barrier to bacteria and to liquid water.

Accordingly the present invention provides a wound dressing which comprises an absorbent layer and a wound facing layer which wound dressing is characterised in that the absorbent layer comprises an open cell foam of a hydrophilic polymer and the wound facing layer comprises a conformable net of elastomer coated with adhesive on its wound facing surface.

Desirably the wound dressing of the invention has an outer layer of a moisture vapour transmitting film. Therefore in another aspect the present invention provides a wound dressing which comprises an outer layer, an intermediate absorbent layer and a wound facing layer which dressing is characterised in that the outer layer comprises a conformable moisture vapour transmitting layer, the intermediate absorbent layer comprises an open cell foam of hydrophilic polymer and the wound facing layer comprises a net of elastomer coated with adhesive on its wound facing surface.

Suitable adhesives are those which do not adhere to the moist surface of the healing wound.

Alternately, the elastomer net-adhesive combination may be replaced by an adhesive layer, pattern spread in a similar configuration such that is forms a discrete wound facing layer.

Thus, in a further aspect the present invention provides a wound dressing which comprises an absorbent layer and a wound facing layer which wound dressing is characterised in that the absorbent layer comprises an open cell foam of a hydrophilic polymer and the wound facing layer comprises an adhesive layer, pattern spread in a conformable net-like configuration onto the absorbent layer.

Desirably this aspect of the invention also has an outer layer of a moisture vapour transmitting film. Thus, in yet another aspect the present invention provides a wound dressing which comprises an outer layer, an intermediate absorbent layer and a wound facing layer which dressing is characterised in that the outer layer comprises a conformable moisture vapour transmitting layer, the intermediate absorbent layer comprises an open cell foam of hydrophilic polymer and the wound facing layer comprises an adhesive layer, pattern spread in a conformable net-like configuration onto the absorbent layer.

Normally the layers of the dressing of this invention are attached in a contiguous and co-extensive manner;

that is the dressing is normally provided in the form of a laminate.

Materials for use in the dressings of the invention and methods of preparing these materials are disclosed in U.S. patent application Ser. Nos. 345,488 and 345,550 the contents of which are incorporated herein by cross reference.

Wound dressings of the invention can suitably have a moisture vapour transmission rate of 300 to 5000 grams and preferably 500 to 2000 grams/square meter/24 hours at 37.5° C. at 100% to 10% relative humidity difference. It has been found that such moisture vapour transmission rates will allow the wound under the dressing to heal under moist conditions without causing the skin surrounding the wound to macerate.

The adhesive coating on the wound facing layer of dressings of the invention then allows these dressings to be adhered to the skin around the wound site and to be maintained in position over the wound without the use of additional strapping or bandaging means. The adhesive coating should not adhere to the moist surface of a healing wound.

Suitable adhesive coatings for the wound facing layer of dressings of the invention have a thickness of 15 microns to 75 microns and preferably a thickness of 25 to 50 microns. Suitable adhesives for the wound facing layer can be any of those pressure sensitive adhesives normally used for adhesive surgical or medical dressings. Preferred pressure sensitive adhesives comprise acrylate ester copolymers and polyvinyl ethyl ether adhesives. Favoured adhesives of this type are disclosed in the aforementioned patent application.

The conformable net of elastomer dressing of the invention allows wound exudate to pass to the absorbent layer but prevents the absorbent layer making direct contact with the wound surface.

The net used in this invention is preferably an integral net, that is a net with strands and junctions which have been formed integrally during manufacture.

Preferably the net is sufficiently conformable to allow the wound dressing to conform with the body contours and thereby maintain overall contact with the wound surface to ensure that exudate from the wound is absorbed.

It is also desirable that the net should be sufficiently elastically extensible to adjust to any dimensional changes in the absorbent layer which may occur, for example, by expansion on liquid uptake.

Suitable nets will have elongation at break of 100% to 800% desirably 200% to 750% and preferably 300% to 700% when measured as a 2.5 cm wide strip at a 30 cm/minute strain rate at 20° C.

Normally the net of elastomer is made of a pharmaceutically acceptable water insoluble elastomer.

Suitable elastomers include polyurethane, polybutadiene and the like. Preferred polyurethanes and polybutadiene elastomers are disclosed in the aforementioned patent applications.

The net of the wound facing layer of the dressing of the invention can have any convenient form depending on the chosen arrangement of strand, junctions and aperture areas and also their shapes and relative size.

Suitable forms of net for the dressings of the invention and the physical characteristics of these nets including preferred numbers and sizes of the net apertures, areas of the voids (apertures), thicknesses and weights of the net are disclosed in the aforementioned patent applications.

Alternatively, the elastomer net-adhesive combination may be replaced by an adhesive layer, pattern spread in a similar configuration such that is forms a discrete wound facing layer.

Suitable favoured and preferred adhesives in this aspect of the invention are as so described for the net coating adhesives hereinbefore.

The net-like adhesive layer is preferably distensible such that distortion of the dressing does not occur during dimensional changes in the absorbent layer which may occur, for example by expansion in liquid uptake or on body surface movement.

The conformable hydrophilic polymer open cell absorbent layer used in dressings of the invention is capable of absorbing wound exudate for example from a burn. It is desirable that the hydrophilic polymer foam layer absorbs the wound exudate rapidly as this enhances the low adherency properties of the absorbent pad. Such rapid absorption prevents undesirable pooling of exudate between the dressing and the wound.

The ability of open cell hydrophilic polymer foam layers to absorb and retain fluids depends to some extent on the size of the foam cells, the porosity of the foam and the thickness of the foam layer. Apt sizes of the foam cells, cell membrane opening areas and thicknesses of the foam are disclosed in the aforementioned patent applications.

The use of such foams of hydrophilic polymer in the absorbent pad of dressings of the invention can allow the wound to be maintained in a moist condition even when the exudate produced has been absorbed and removed from the wound surface.

Favoured hydrophilic polymer foams are hydrophilic polyurethane and especially those which are made of crosslinked hydrophilic polyurethane. Preferred foams can be made by reacting a hydrophilic isocyanate terminated polyether prepolymer with water. Favoured hydrophilic polyurethane foams of this type includes those known as Hypol foams. Hypol foams can be made from Hypol hydrophilic prepolymers marketed by W R Grace and Co.

The conformable moisture vapor transmitting outer layer of dressings of the invention when present can be continuous or discontinuous.

A preferred moisture vapour transmitting outer layer is a continuous conformable film. The continuous moisture vapour transmitting conformable film outer layer of the wound dressing of the invention may be used to regulate the moisture loss from the wound area under the dressing and also to act as a barrier to bacteria so that bacteria on the outside surface of the dressing cannot penetrate to the wound area.

Suitable continuous conformable films will have a moisture vapour transmission rate of 300 to 5000 grams preferably 500 to 2000 grams/square meter/24 hrs at 37.5° C. at 100% to 10% relative humidity difference. It has been found that such moisture vapour transmission rates of the continuous film allow the wound under the dressing to heal under moist conditions without causing the skin surrounding the wound to macerate.

Suitable moisture vapour transmitting continuous films can be made of polyurethane or copolymers of alkoxy alkyl acrylates or methacrylates such as those disclosed in British Patent No. 1,280,631. Apt polyurethanes and polyurethane films are disclosed in the aforementioned patent applications.

The continuous moisture vapour transmitting film can be a conformable polyurethane incompatible polymer blend film containing voids. Suitable conformable polyurethane blend films are disclosed in United Kingdom Patent Application GB 2081721A.

Suitable conformable discontinuous moisture vapour transmitting outer layers for use in the dressings of the invention can be any of those normally used for wound dressings. Such backing layers include conformable porous and microporous films, non-woven fabrics, nets and woven and knitted fabrics.

Preferred discontinuous outer layers include extensible apertured non-woven fabrics and elastomer nets. Such preferred materials are disclosed in the aforementioned patents.

An apt conformable moisture vapour transmitting outer layer comprises a microporous film. The conformable film microporous outer layer of the wound dressing of the invention may be used to regulate the moisture loss from the wound area under the dressing and also to act as a barrier to bacteria to delay or prevent bacteria on the outside surface of the dressing penetrating to the wound area.

Suitable conformable microporous films will have a moisture vapour transmission rate of 300 to 5000 grams preferably 500 to 4000 grams/square meter/24 hrs at 37.5° C. at 100% to 10% relative humidity difference.

Suitable conformable microporous films have pore diameter of less than 2 microns desirably less than 0.6 microns and preferably less 0.1 microns. Such microporous films should have pore diameter of greater than 0.01 microns.

Suitable conformable microporous films have a thickness of 25 to 400 microns preferably 50 to 300 microns. The conformable microporous film will be made of a polymer.

Suitable polymers include plasticised polyvinyl chloride polyurethane elastomers and ethylene vinyl acetate copolymer elastomers.

A favoured conformable microporous film comprises a microporous plasticised polyvinyl chloride film having an average pore diameter of less than 2 microns, a thickness of 250 to 300 microns and a moisture vapour transmission rate of 3000 to 5000 g/m$^2$/24 hours at 37.5° C. at a relative humidity difference of 100% to 10% relative humidity.

The conformable moisture transmitting outer layer of wound dressings of the invention may also comprise a moisture vapour transmitting adhesive layer to bond the outer layer to the intermediate layer of open cell foam. These adhesive layers can be continuous or discontinuous.

Suitable adhesives which are moisture vapour transmitting as a continuous layer include various acrylate ester copolymer and polyvinyl ether pressure sensitive adhesives for example as disclosed in British Patent No. 1280631. Favoured pressure sensitive adhesives comprise copolymers of an acrylate ester with acrylic acid for example as disclosed in United Kingdom Application GB 2070631.

Suitable discontinuous adhesive layers for use on the backing layer of dressings of the invention can be any of those conventionally used for wound dressings. Such discontinuous adhesive layers can include porous, microporous or pattern spread layers.

The wound dressing of the invention can contain a topically effective medicament. Most suitably the medicament is an antibacterial agent. Preferably the antibacterial agent is a broad spectrum antibacterial agent such as a silver salt of example silver sulphadiazine, an acceptable iodine source such as povidone iodine (also called polyvinyl pyrrolidone iodine or PVP/I), chlorhexidine salts such as the gluconate, acetate, hydrochloride or the like salts or quaternary antibacterial agents such as bensalkonium chloride or the like.

The medicament can be located in the foam layer or in the adhesive coating.

The medicament is preferably located in the foam layer of the dressing.

Preferred amounts of suitable medicaments for incorporation into the foam layer of the dressing of the invention are disclosed in the aforementioned patent applications.

The wound dressing of this invention may be in any convenient form of shape or size. In a preferred form the wound dressing is a pad of rectangular shape. In another preferred form the wound dressing can be an elongate strip which may be used as a bandage or may be used to prepare smaller dressings.

It is desirable that the wound dressing of this invention are sterile. The wound dressing of the invention is advantageously provided in bacteria impervious pouches. Such packed forms can be prepared under aseptic conditions or alternatively sterilised after packing by a conventional procedure. A favoured sterilisation procedure is heat sterilisation, for example, by steam. Other favoured procedures are ethylene oxide sterilisation or gamma irradiation.

In another aspect the present invention provides a process of making a wound dressing of the invention which comprises bringing together an absorbent layer comprising an open cell foam of a hydrophilic polymer and wound facing layer comprising a conformable net of elastomer coated with adhesive on its wound facing surface.

Normally the bringing together of the layers will be a lamination process. Such lamination processes can also be used to form wound dressings with a conformable moisture vapour transmitting outer layer.

The previously formed individual layers can be formed into a laminate by bonding layers together in one or more laminating processes. Suitable bonding methods include heat sealing or adhesive bonding providing that the adhesive layer does not significantly reduce the moisture vapour transmitting rate of the dressing or the passage of wound exudate into the dressing from the undesirable wound surface.

In the lamination process of the invention one or more layers can be formed into contact with a previously formed layer.

The preferred bonding method for forming the film/foam or film/foam/net laminate of the invention is heat sealing. The net and film layers can be heat sealed to the foam layer by heat and pressure in a conventional manner in one or more laminating processes. An apt heat sealing process comprises passing the net or film layer in contact with the foam layer through the nip of a heated metal roller and rubber roller under low pressure. To ensure that the net or film is in a heat softened state it is desirable that the net or film layer is adjacent to the heated metal roller.

When the net has been formed on an embossed film coating sheet, it is preferred that the net is supported on its embossed film casting sheet during the heat lamination process. It has been found with this arrangement that the supported net has less tendency to be compressed and 'flattened' into the surface of the foam by heat and pressure of laminating process thus ensuring that the net is a discrete layer on the foam surface.

The adhesive can be coated onto the wound facing surface of the net before, during or after the net has been laminated to the foam layer. In a preferred process the adhesive in a flowable state is last into the recesses of a release coating surface having a pattern of discrete raised areas and interconnected recessed areas and the net layer formed in a similar manner on the adhesive layer.

Preferred casing surfaces are embossed polymer sheets. Suitable embossed polymer sheets are disclosed in the aforementioned patent applications.

The adhesive coated net on its embossed polymer sheet carrier can conveniently be bonded to the foam layer by heat sealing.

In a further aspect the present invention provides a process of making a wound dressing of the invention which comprises pattern spreading an adhesive layer in a conformable net-like configuration onto an absorbent layer comprising an open cell foam of a hydrophilic polymer.

Such pattern spreading may be effected conventionally.

In a continuous process the wound dressing can be made in the form of a continuous strip which is then cut up in suitable size dressings.

Processes for forming the materials used in dressings of the invention including the preferred hydrophilic foam layer, the preferred polyurethane net layers, the preferred continuous polyurethane outre layers and the preferred polyvinyl ethyl ether and acrylate ester copolymer adhesive coatings and laminates of these materials are disclosed in the aforementioned patent applications.

Suitable microporous films for the outer layer of a wound dressing of the invention can be made by the method disclosed in British Patent No. 884,232.

The adhesive surface of wound dressings of the invention will usually be provided with a release coated protector. The release coated protector can be the embossed sheet carrier used for forming the adhesive coated net layer. Other suitable release coated protectors include silicone coated release papers such as Steralease paper nos. 15 and 67 made by Sterling Coated Papers Limited.

The invention is now illustrated by the following examples.

EXAMPLE 1

A net-foam dressing of the invention was formed by preparing a net of elastomer coated with adhesive and laminating the uncoated surface of the net to an open cell foam of a hydrophilic polymer.

PREPARATION OF ADHESIVE COATED NET

A solution (30% in acetone) of an acrylic ester copolymer adhesive was cast into the recesses of a silicone release coated melt embossed polypropylene sheet (polypropylene containing 40% by weight of chalk filler reference PXC 4999 available from ICI Plastics Limited) by means of a blade over soft bed coating technique. The sheet had a melt embossed pattern of 4 per cm raised areas in diagonal rows (45°) of square truncated pyramids 2 mm wide at their base, 1.42 mm wide at their top and 0.5 mm high with sides sloping to a conical angle of 60°. The acrylate ester copolymer consisted of a copolymer of 47 parts by weight of n-butyl acrylate, 47 parts by weight of 2-ethylhexyl acrylate and 6 parts by weight of acrylic acid with an intrinsim viscosity of 1.9 dl/g polymerised in acetone according to the general method given in British Patent Application GB 2070631.

The adhesive coating was dried in a heated oven to give a dry weight per unit area of 50 g/m$^2$ (approximately 50 microns thick).

A solution containing 20% by weight of Estane 5714F (available from B.F. Goodrich) in 60/40 (weight by weight) mixture of tetrohydrofuran/acetone was cast into adhesive coated recesses of the emobossed film and the wet cast net on the embossed film dried by passage through a hot air oven at a temperature of 80° C. for two minutes.

PREPARATION OF THE ABSORBENT LAYER

Using a two component dispensing Vari-o-mix (supplied by Prodef Engineering Limited) a foaming mixture was formed by mixing Hypol F H P 2002 and Brig 72 (1% aqueous solution) in the ratio of 1:2. The foaming mixture was put into the coating head by means of an output nozzle in the form of a 15 cm wide 'fishtail die' and coated onto a silicone coated release paper (Stearalese No. 46 available from Sterling Coated Papers Limited) by means of a knife over roller coating head set at a gap of 1 mm. The cast foam was dried by passage through an air circulating oven at a temperature of 50° C. for 5 minutes. The cast hydrophilic polyurethane foam had a thickness of 2 mm.

PREPARATION OF LOW ADHERENCY WOUND DRESSINGS

The polyurethane adhesive coated net on its coated release embossed sheet was heat laminated to the hydrophilic polyurethane foam on its silicone coated release casting paper by passing the layers between the nip of a silicone rubber roller and a steel roller heated by circulating oil to a temperature of 85° C. The embossed sheet carrying the polyurethane net was fed against the heated steel roller to ensure that the net was in a heat softened condition prior to its lamination to the foam.

The silicone release carrier paper was removed from the foam surface to give a laminate strip and the strip cut into suitable size dressings. The net had a weight per unit area of 25 g/m$^2$ and had 4 per/cm apertures of approximately 1.4 mm in size.

EXAMPLE 2

The net-foam laminate of Example 1 was laminated to a conformable polyurethane film outer layer (Estane 5714F) of weight 12.5 g/m$^2$) by passing the film, on a silicone release coated paper carrier, in contact with the foam side of the laminate through the nip of silicone rubber roller and a steel roller heated by circulating oil to a temperature of 120° C. The silicone release coated paper carrying the polyurethane film was fed against the heated steel roller to ensure that the film was in a heat softened condition prior to its lamination to the foam.

The silicone paper was removed from the film surface to give a laminate strip and the strip cut into suitable size dressings.

DEMONSTRATION OF EFFECTIVENESS

Absorbency Testing

A dressing formed as described in Example 1 was placed with the net-carrying surface of the foam in contact with horse serum. The serum was available through an orifice 1 cm in diameter at zero hydrostatic pressure. The penetration of the serum was followed by observation and by weighing the dressing before and at intervals during the absorption process. Initially the rate of absorption was slow but increased rapidly so that, after 60 minutes from the start of the experiment, the pad was observed to be saturated and contained 10 g of serum, as measured by the weight difference between the start and end of the experiment.

The experiment showed that the absorption capacity of the foam was not restricted by the presence of a net on one surface and a film on the other.

DEMONSTRATION OF EFFECTIVENESS

Moisture Vapour Permeability (MVP) Determination

Discs of the dressing material that is a laminate of Adhesive/net/foam, to be tested are clamped over Payne Permeability Cups (flanged metal cups) using sealing rings and screw clamps. The exposed surface of the test sample is 10 cm$^2$. Each cup contains approximately 10 ml of distilled water.

After weighing the cups are placed in a fan assisted electric oven maintained at 37.5° C. The relative humidity within the oven is maintained at approximately 10% by placing 1 kg of anhydrous 3–8 mesh calcium chloride on the floor of the oven.

The cups are removed after 24 hours, allowed to cool for 20 minutes and reweighed. The MVP of the test material is calculated from the weight loss and expressed in units of grams of weight per square meter per 24 hours, at 37.5° C. at 100–10% relative humidity difference.

The results were as follows:

| Sample | Moisture vapour permeability (g/m$^2$/24 hrs) |
|---|---|
| Dressing material (ex Example 1) | 2252, 2178, 2294, 2282 |

We claim:

1. A wound dressing which consists essentially of a low adherency wound facing layer, an absorbent layer and an outer layer, wherein said low adherency wound facing layer has a wound contacting, first adhesive coating over its wound facing surface, said low adherency wound facing layer comprises a conformable apertured film, a conformable net of elastomer or an adhesive layer pattern spread in a conformable net-like configuration, the absorbent layer comprises a conformable hydrophilic foam and the outer layer is a continuous or discontinuous moisture vapour transmitting conformable backing layer which has a layer of a second adhesive on one surface thereof, at least one of said backing layer and said second adhesive layer being continuous to provide a barrier to bacteria and to liquid water.

2. A wound dressing according to claim 1 wherein the absorbent layer comprises an open cell foam of a hydrophilic polymer.

3. A wound dressing according to claim 2 wherein the hydrophilic polymer is a hydrophilic polyurethane.

4. A wound dressing according to claim 1 wherein the wound facing layer comprises a conformable net of elastomer.

5. A wound dressing according to claim 1 wherein the wound facing layer comprises an adhesive layer, pattern spread in a conformable net-like configuration onto the absorbent layer.

6. A wound dressing according to claim 1 wherein the first adhesive is an acrylate ester copolymer pressure sensitive adhesive or a polyvinyl ethyl ether pressure sensitive adhesive.

7. A wound dressing according to claim 6 wherein the first adhesive is an acrylate ester polymer pressure sensitive adhesive or a polyvinyl ethyl ether pressure sensitive adhesive, and has a thickness of 25 to 50 microns.

8. A wound dressing according to claim 1 wherein the outer layer comprises a conformable moisture vapour transmitting layer, the intermediate absorbent layer comprises an open cell foam of hydrophilic polymer and the wound facing layer comprises an adhesive layer, pattern spread in a conformable net-like configuration onto the absorbent layer.

9. A wound dressing according to claim 1 wherein the outer layer is a continuous conformable film.

10. A wound dressing which consists essentially of a low adherency wound facing layer, and an absorbent layer said low adherency wound facing layer having a wound contacting first adhesive coating over its wound facing surface, wherein said low adherency wound facing layer comprises a conformable aperture film, a conformable net of elastomer or an adhesive layer pattern spread in a conformable net-like configuration, and the absorbent layer comprises a conformable hydrophilic foam.

* * * * *